(12) United States Patent
Bechyne et al.

(10) Patent No.: US 6,913,146 B2
(45) Date of Patent: Jul. 5, 2005

(54) INTERLABIAL PAD PACKAGING

(75) Inventors: Kami L. Bechyne, Appleton, WI (US); James D. McManus, Appleton, WI (US); Emily M. Moe, White Bear Lake, MN (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 35 days.

(21) Appl. No.: 10/043,895

(22) Filed: Nov. 9, 2001

(65) Prior Publication Data

US 2003/0089633 A1 May 15, 2003

(51) Int. Cl.7 ............................................. A61L 15/00
(52) U.S. Cl. ........................................ 206/440; 206/494
(58) Field of Search .......................... 206/38, 440, 494, 206/581; 150/147, 149; 383/38, 40

(56) References Cited

U.S. PATENT DOCUMENTS

| | | |
|---|---|---|
| 900,751 A | 10/1908 | Lockwood |
| 1,671,825 A | 5/1928 | Johnson |
| 1,750,375 A | 3/1930 | Vinciguera |
| 2,305,402 A | 12/1942 | Avery et al. |
| 2,573,309 A | 10/1951 | Chipkevich |
| 2,603,266 A | 7/1952 | Carroll |
| 2,750,033 A | 6/1956 | Pickens |
| 2,870,955 A | 1/1959 | Brady et al. |
| 3,062,371 A | 11/1962 | Patience |
| 3,070,280 A | 12/1962 | Richmond |
| 3,160,273 A | 12/1964 | Reuther et al. |
| 3,310,225 A | 3/1967 | Hoblit |
| 3,314,464 A | 4/1967 | Veilleux |
| 3,320,863 A | 5/1967 | Ells et al. |
| 3,338,019 A | 8/1967 | Trewella et al. |
| 3,405,861 A | 10/1968 | Bush |
| 3,420,433 A | 1/1969 | Bostwick |
| 3,557,853 A | 1/1971 | Jones |
| 3,670,876 A | 6/1972 | Davis |
| 3,674,195 A | 7/1972 | Stone |
| 3,730,338 A | 5/1973 | Chesky |
| 3,858,790 A * | 1/1975 | Humphrey ................... 229/72 |
| 3,982,687 A | 9/1976 | Auer et al. |
| 3,990,872 A | 11/1976 | Cullen |
| 4,073,950 A | 2/1978 | Hansen et al. |
| 4,131,195 A | 12/1978 | Worrell |
| 4,192,420 A | 3/1980 | Worrell, Sr. et al. |
| 4,276,982 A | 7/1981 | Sibrava et al. |
| 4,286,639 A | 9/1981 | Murphy |
| 4,441,613 A | 4/1984 | Hain et al. |
| 4,460,088 A | 7/1984 | Rugenstein et al. |
| 4,502,599 A | 3/1985 | Perecman |
| 4,546,029 A | 10/1985 | Cancio et al. |
| 4,550,855 A | 11/1985 | Harrison |

(Continued)

FOREIGN PATENT DOCUMENTS

| | | |
|---|---|---|
| CA | 2025856 | 3/1991 |
| CA | 2 109 782 | 5/1995 |
| DE | 39 23 839 A1 | 10/1990 |
| EP | 0 419 770 A1 | 4/1991 |
| EP | 1 043 004 A2 | 10/2000 |
| FR | 1 482 194 | 4/1966 |
| WO | WO 94/00362 | 1/1994 |
| WO | WO 98/18682 | 5/1998 |
| WO | WO 98/57610 | 12/1998 |
| WO | WO 99/26576 | 6/1999 |
| WO | WO 02/08087 A2 | 1/2002 |

OTHER PUBLICATIONS

PCT/US01/30964 International Search Report from the European Patent Office dated May 8, 2002.
PCT/US01/44975 International Search Report from the European Patent Office dated May 8, 2002.

Primary Examiner—David T. Fidei
(74) Attorney, Agent, or Firm—Senniger, Powers, Leavitt & Roedel

(57) ABSTRACT

A package of individually packaged interlabial pads.

9 Claims, 7 Drawing Sheets

U.S. PATENT DOCUMENTS

| | | |
|---|---|---|
| 4,556,146 A | 12/1985 | Swanson et al. |
| 4,679,693 A | 7/1987 | Forman |
| 4,700,841 A | 10/1987 | Padgett, Jr. et al. |
| 4,713,839 A | 12/1987 | Peppiatt |
| 4,739,879 A | 4/1988 | Nakamura |
| 4,743,245 A | 5/1988 | Lassen et al. |
| 4,785,940 A | 11/1988 | Wilson |
| 4,786,190 A | 11/1988 | Van Erden et al. |
| 4,834,241 A | 5/1989 | Southern |
| 4,838,327 A | 6/1989 | Ambler et al. |
| 4,917,675 A | 4/1990 | Taylor et al. |
| 4,934,535 A | 6/1990 | Muckenfuhs et al. |
| 4,948,028 A | 8/1990 | Vollowitz |
| 4,964,859 A | 10/1990 | Feldman |
| 4,966,286 A | 10/1990 | Muckenfuhs |
| 4,979,613 A | 12/1990 | McLaughlin et al. |
| 5,046,620 A | 9/1991 | Barabino |
| 5,048,687 A | 9/1991 | Suzuki et al. |
| 5,050,742 A | 9/1991 | Muckenfuhs |
| 5,054,619 A | 10/1991 | Muckenfuhs |
| 5,065,868 A | 11/1991 | Cornelissen et al. |
| 5,076,465 A | 12/1991 | Lawson |
| 5,082,112 A | 1/1992 | Dunklee |
| 5,242,057 A | 9/1993 | Cook et al. |
| 5,261,531 A | 11/1993 | Nieves |
| 5,358,171 A | 10/1994 | Focke |
| 5,391,136 A | 2/1995 | Makowka |
| 5,413,568 A | 5/1995 | Roach et al. |
| D360,577 S | 7/1995 | van Loo |
| 5,476,323 A | 12/1995 | Gold |
| D365,981 S | 1/1996 | Sullivan |
| 5,560,798 A | 10/1996 | Brusky |
| 5,569,230 A | 10/1996 | Fisher et al. |
| 5,579,916 A | 12/1996 | Manko |
| 5,639,523 A | 6/1997 | Ellis |
| 5,655,842 A | 8/1997 | Hagino |
| 5,730,294 A | 3/1998 | Blosser et al. |
| 5,778,954 A * | 7/1998 | Sullivan et al. ............. 150/143 |
| 5,884,771 A | 3/1999 | McCormick |
| 5,951,505 A | 9/1999 | Gilman et al. |
| 5,954,201 A | 9/1999 | Finch et al. |
| 5,971,153 A | 10/1999 | Bauer et al. |
| 5,996,797 A | 12/1999 | Flaig |
| 6,015,045 A | 1/2000 | Joseph et al. |
| 6,039,175 A | 3/2000 | Wright |
| 6,041,928 A | 3/2000 | Jousinen et al. |
| 6,059,100 A | 5/2000 | Jones |
| 6,115,997 A | 9/2000 | Burrow et al. |
| 6,126,009 A | 10/2000 | Shiffler et al. |
| 6,168,022 B1 | 1/2001 | Ward et al. |
| 6,257,473 B1 | 7/2001 | Ringelstetter |
| 6,338,572 B1 | 1/2002 | Schneck |
| 2002/0063076 A1 * | 5/2002 | Kolterjohn et al. ......... 206/440 |

* cited by examiner

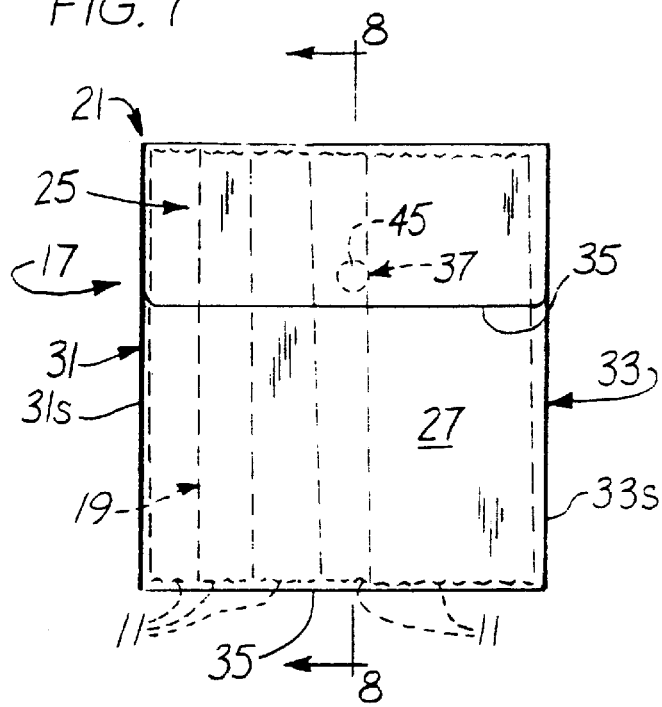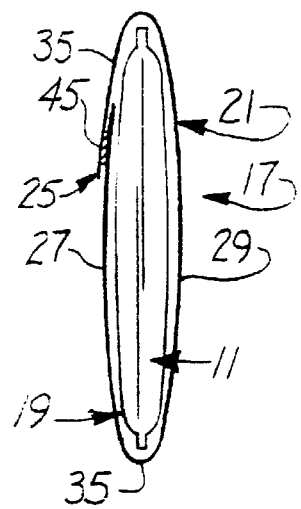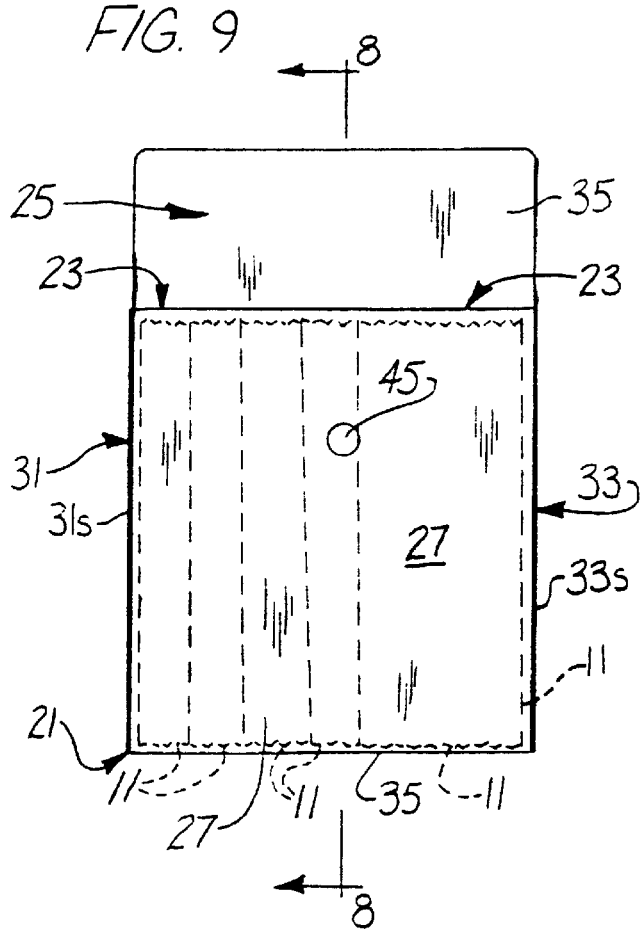

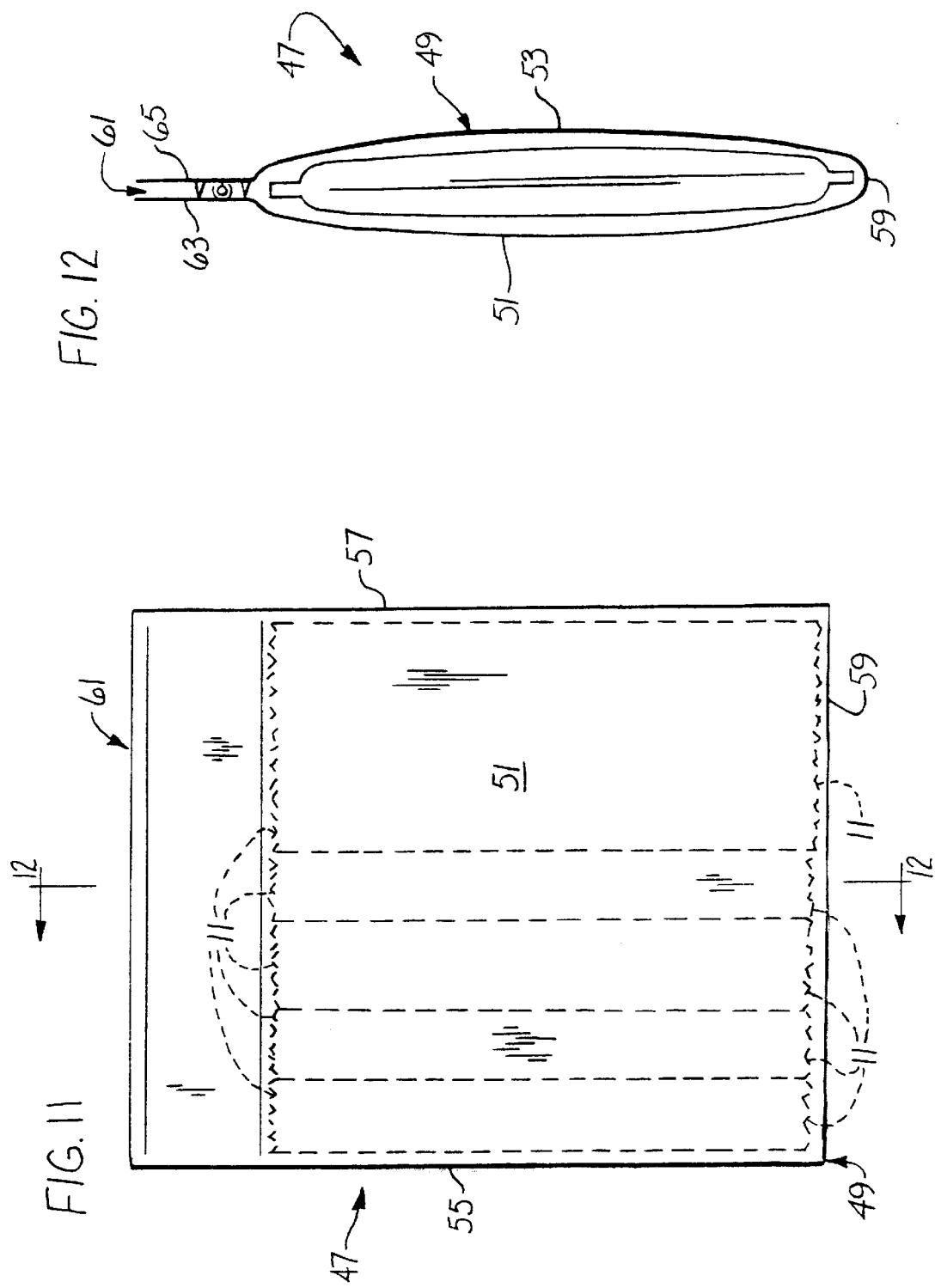

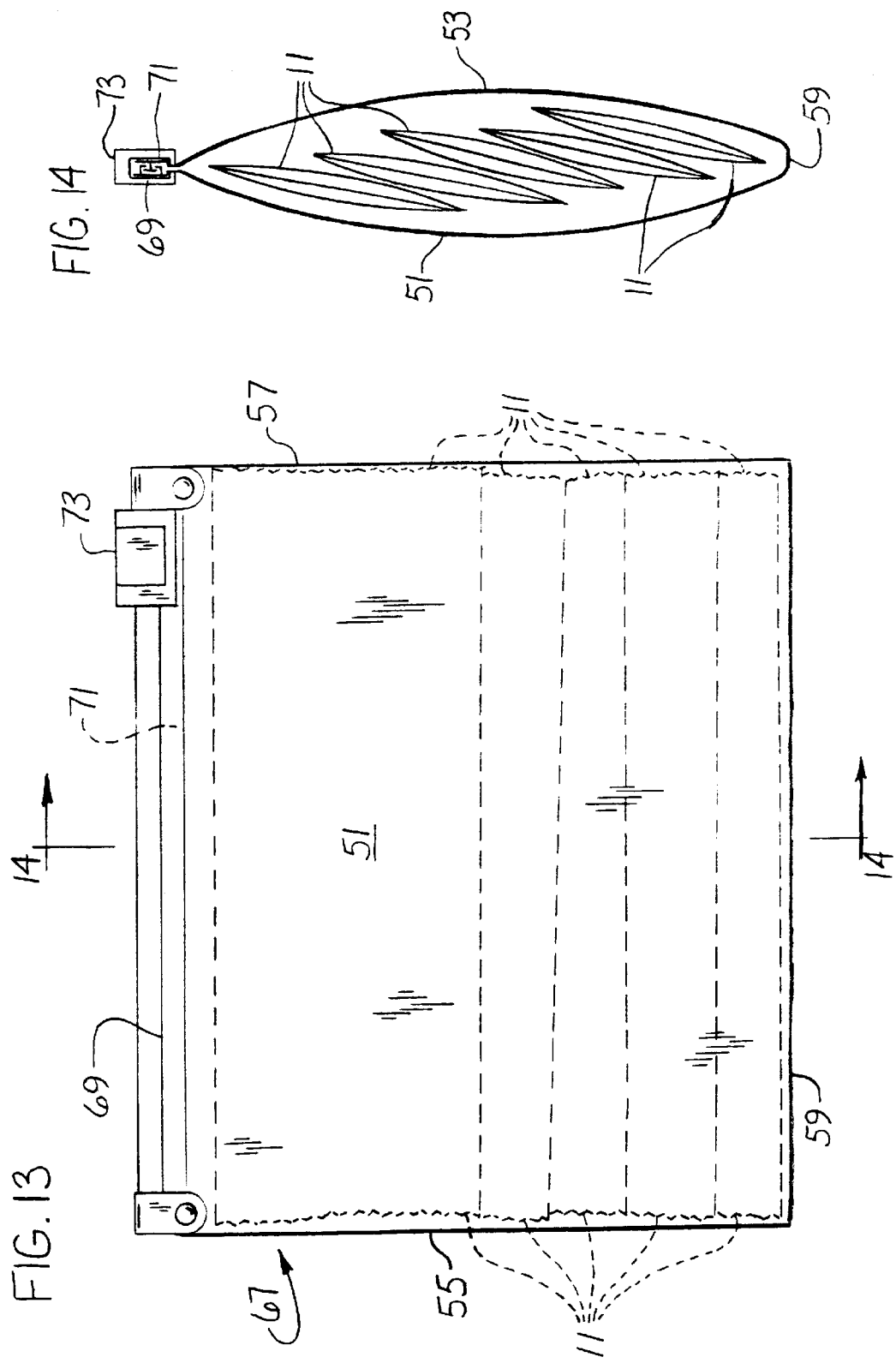

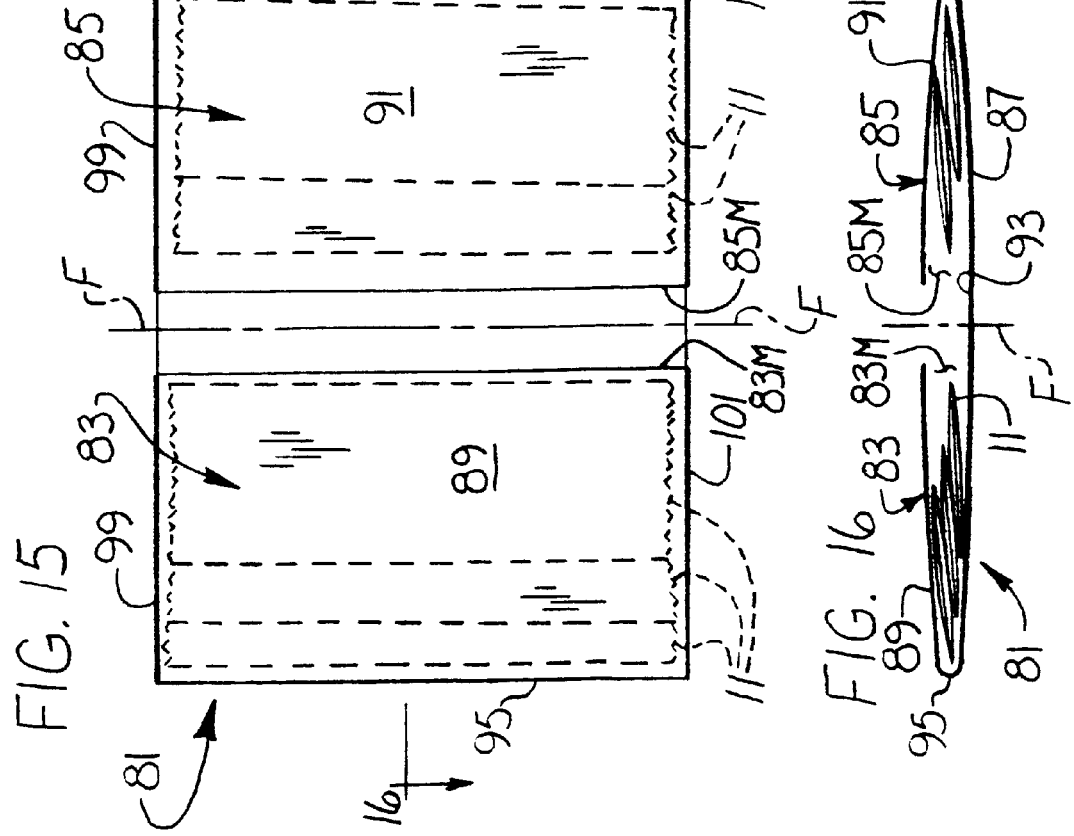

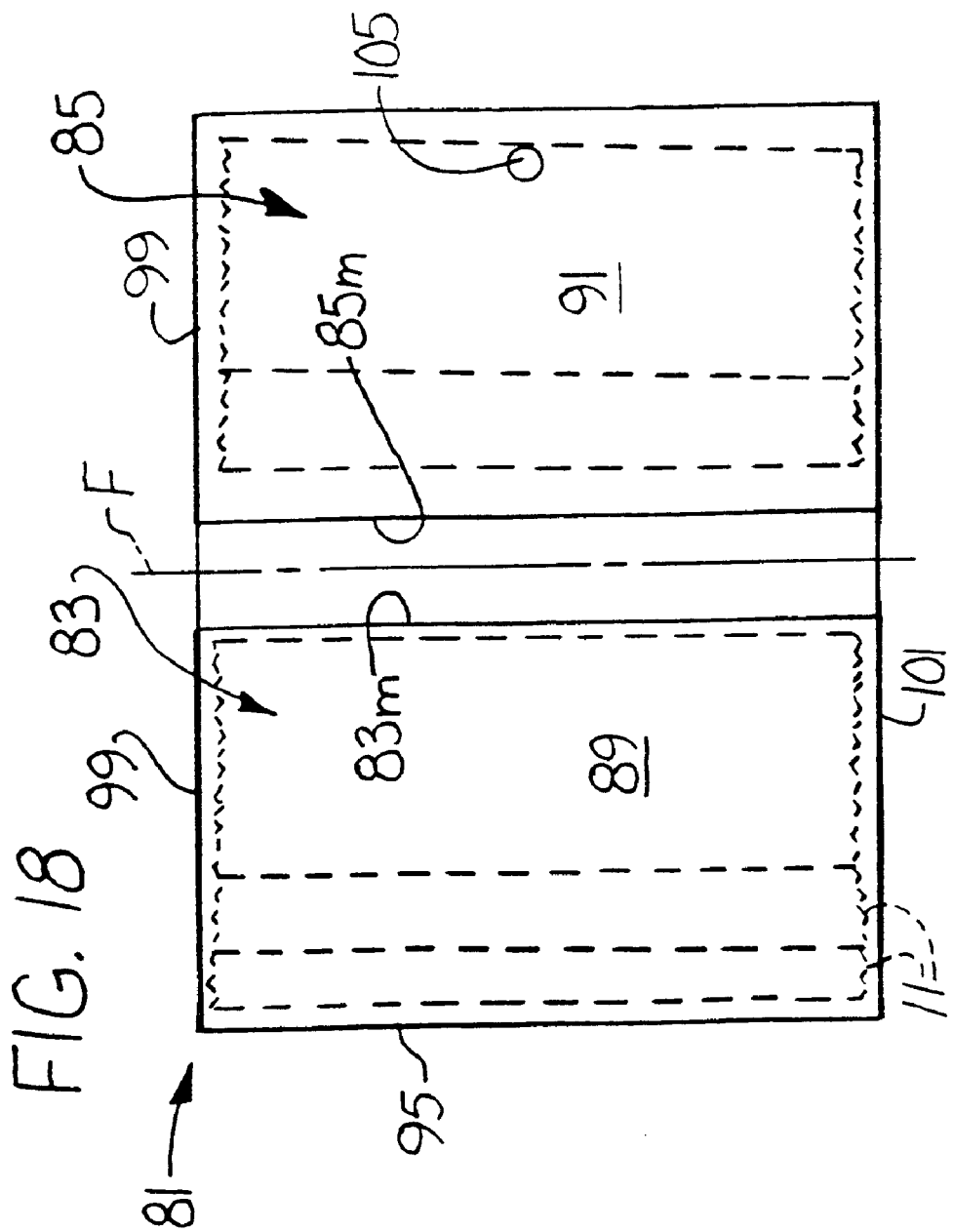

INTERLABIAL PAD PACKAGING

BACKGROUND OF THE INVENTION

This invention relates generally to a package, and more particularly to interlabial pad packaging.

The invention concerns the packaging of interlabial pads of the type shown in U.S. Pat. No. 4,595,392 issued Jun. 17, 1986, entitled "Interlabial Pad", and U.S. Pat. No. 4,673,403 issued Jun. 16, 1987, entitled "Method and Pad Allowing Improved Placement of Catamenial Device". In addition, the invention is applicable to the packaging of other interlabial pads.

Interlabial pads like other absorbent feminine care products (e.g., tampons, panty liners and feminine napkins) are intended to be carried about in purses, backpacks and briefcases until needed. Unfortunately, these containers do not always provide a hygienic environment for the pads, and thus the pads can become dirty and/or damaged. Further, the pads can become scattered about in the containers so they are difficult to find when needed. Although packages have been developed to hold other absorbent feminine care products (e.g., the packages described in co-pending U.S. patent application Ser. Nos. 09/713,604, 09/713,496, 09/713,565, 09/713,497, and 09/713,596, all of which were filed on Nov. 15, 2000, and are hereby incorporated by reference; and application Ser. Nos. 09/917,540, and 09/916,795, both of which were filed on Jul. 27, 2001, and are hereby incorporated by reference), there is a need for packaging for interlabial pads.

BRIEF SUMMARY OF THE INVENTION

In general, the invention comprises a package of interlabial pads for carrying a supply of the pads in hygienic condition in such manner as to maintain them in hygienic condition and to be readily available for use in hygienic condition when needed. The package comprises a receptacle and a supply of pads in the receptacle. The receptacle has an opening through which a pad may be withdrawn for use when needed. Further, the receptacle has a reclosable closure for closing the opening. The closure is closed for carrying the pads in hygienic condition and for continued carrying in hygienic condition of the pads remaining in the receptacle after withdrawal of a pad.

Other features will be in part apparent and in part pointed out hereinafter.

BRIEF DESCRIPTION OF THE DRAWINGS

FIG. 7 is a front elevation of a package of a first embodiment of the present invention in a closed condition, the packaged pads therein shown in dashed lines;

FIG. 8 is a section taken in the plane of line 8—8 of FIG. 7;

FIG. 9 is a front elevation of the package of FIG. 7 in an opened condition;

FIG. 10 is a section taken in the plane of line 10—10 of FIG. 9;

FIG. 11 is a front elevation of a package of a second embodiment of the present invention, the packaged pads therein shown in dashed lines;

FIG. 12 is a section taken in the plane of line 12—12 of FIG. 11;

FIG. 13 is a front elevation of a package of a third embodiment of the present invention, the packaged pads therein shown in dashed lines;

FIG. 14 is a section taken in the plane of line 14—14 of FIG. 13;

FIG. 15 is a front elevation of a package of a fourth embodiment of the present invention in an opened condition, the packaged pads therein shown in dashed lines;

FIG. 16 is a section taken in the plane of line 16—16 of FIG. 15;

FIG. 17 is a front elevation of the package of FIG. 15 in an opened condition; and FIG. 18 is a front elevation of a package of a fifth embodiment of the present invention in an opened condition, the packaged pads therein shown in dashed lines.

Figure 1:
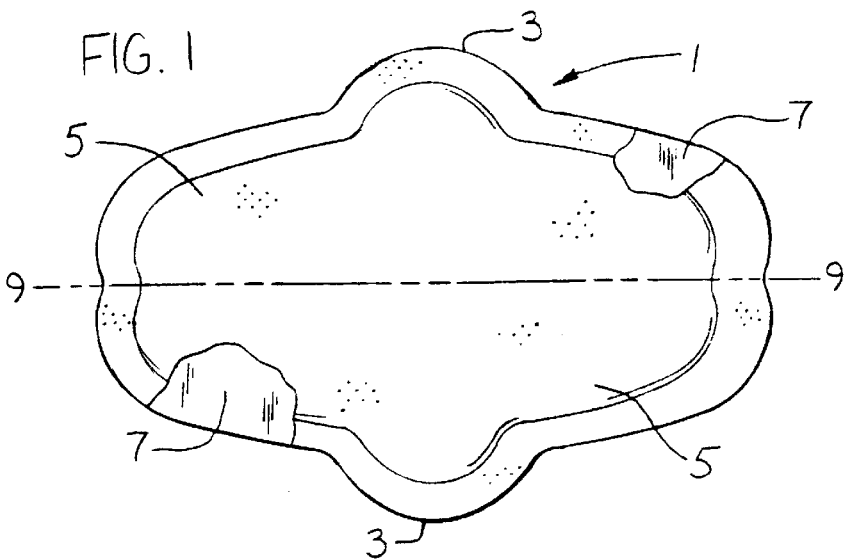
FIG. 1 is a plan view of an interlabial pad such as may be packaged in accordance with this invention, partly broken away to show detail.

In the above-noted sectional views, film is depicted in single-line style rather than in exaggerated thickness with cross-hatching.

Corresponding reference characters indicate corresponding parts throughout the several views of the drawings.

DETAILED DESCRIPTION

Figure 2:
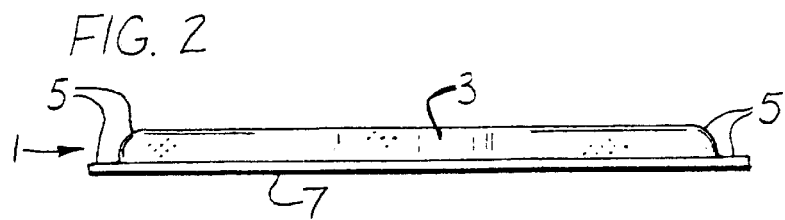
FIG. 2 is a edge view of the interlabial pad.
Figure 3:
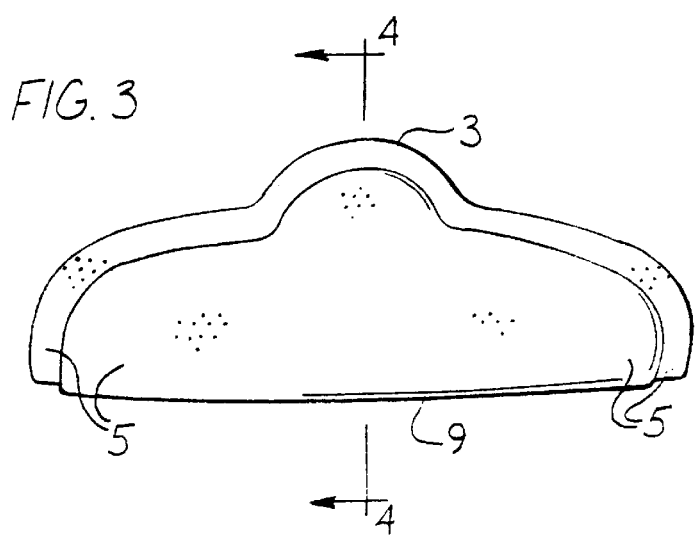
FIG. 3 is a plan view showing the pad folded.
Figure 4:
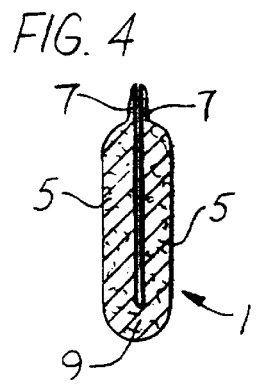
FIG. 4 is a section taken in the plane of line 4—4 of FIG. 3.
Figure 6:
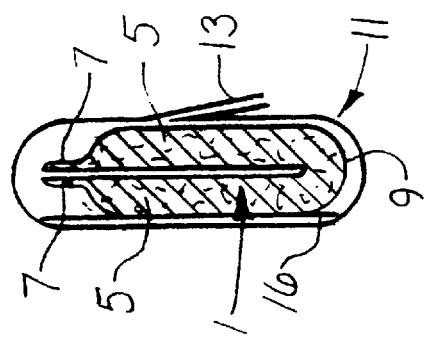
FIG. 6 is a section taken in the plane of line 6—6 of FIG. 5.
Figure 5:
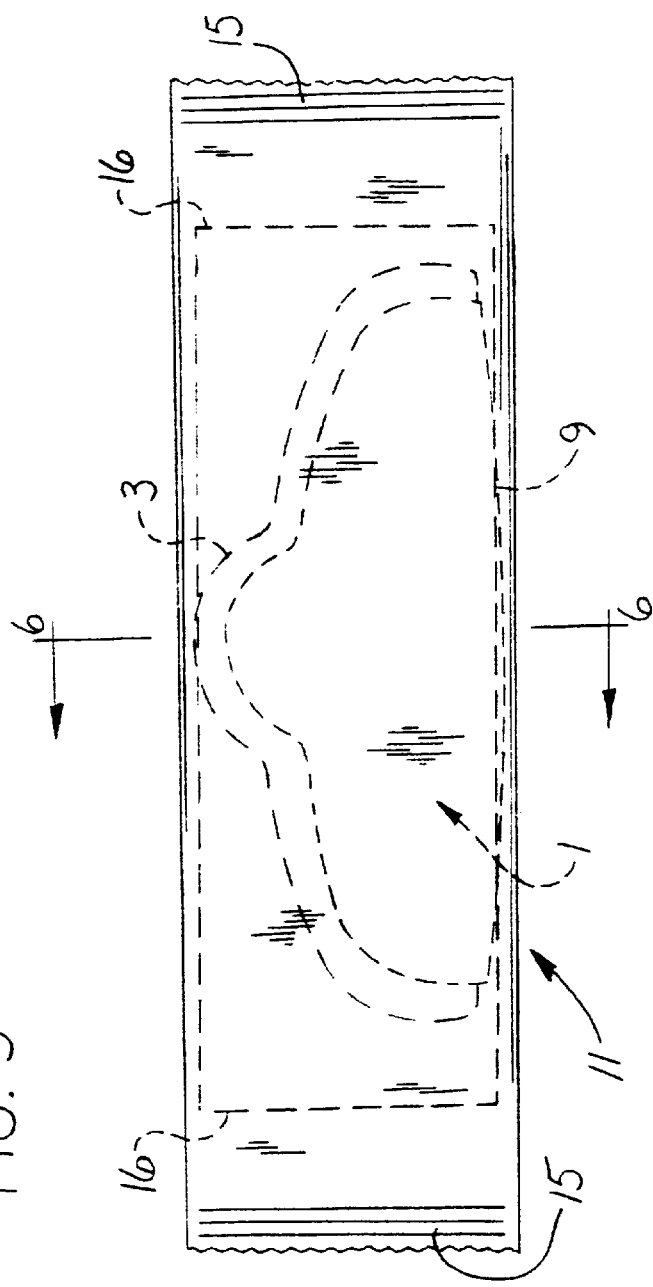
FIG. 5 is a front elevation of hygienic packaging containing the folded pad.

Referring to FIGS. 1 and 2 of the drawings, an interlabial pad is designated in its entirety by the reference number 1. The pad 1, which is exemplary of interlabial pads that may be packaged in accordance with this invention, is generally of the type disclosed in the aforesaid U.S. Pat. Nos. 4,595, 392 and 4,673,403, which are hereby incorporated by reference. In one embodiment, the pad 1 is generally oval and has lateral projections 3. Although the pad 1 may have other dimensions without departing from the scope of the present invention, in one embodiment the pad has an overall width of about 3.4 centimeters (cm) and an overall length of between about 6 cm and about 10 cm. As those skilled in the art will appreciate, the interlabial pad may have other shapes without departing from the scope of the present invention. Although the pad 1 of one embodiment comprises a lamination of a layer 5 of absorbent material on a fluid impervious layer 7 (e.g., plastic film), pads having other configurations including those without an impervious layer are also contemplated. As shown in FIGS. 3 and 4, in one embodiment the pad 1 is folded in half on its major axis as indicated at 9 and, as shown in FIGS. 5 and 6, is individually packaged in an elongate, generally flat sealed hygienic package 11 having a longitudinal seam 13 and end seals 15. In alternative embodiments, it is envisioned that the package 11 may not be sealed or may be omitted entirely. Further, it is envisioned that the pad 1 may be unfolded without departing from the scope of the present invention. Although the package 11 may be made of other materials without departing from the scope of the present invention, in one embodiment the package is made of heat-sealable plastic film and in another embodiment the package is made of paper. The seam 13 and seals 15 may be made by any conventional process such as heat sealing, mechanical sealing or adhesive bonding. Further, it is envisioned that the pad 1 may be sealed in the package 11 with a cardboard backing 16. Although the package 11 may have other dimensions without departing from the scope of the present invention, in one embodiment the package has an overall width of about 4.0 cm and an overall length of between about 8.5 cm and about 12.5 cm.

As illustrated in FIGS. 7 and 8, a package of a first embodiment of the present invention is designated in its entirety by the reference numeral 17. The package 17, carries a supply 19 of the interlabial pads 1 individually wrapped in their respective sealed hygienic packages 11 readily available for use when needed. The package 17 generally comprises a receptacle 21 (e.g., a pocket) having a mouth or opening 23 (see FIG. 10 particularly) through which a pad 1 in its sealed package 11 may be withdrawn for use when needed. The receptacle 21 has a reclosable flap 25 for closing the opening 23. The flap 25 may be closed after a pad 1 is withdrawn to retain the remaining pads in the receptacle 21 until needed.

The receptacle 21 comprises a bag having front and back walls 27 and 29 joined at the sides 31 and 33 and bottom 35 and free from each other at the top to define the opening 23. The flap 25 which is integral with the back wall 29 may be folded over the opening 23 so it overlies the front wall 27. The flap 25 is releasably adhered to the front wall 27 by an adhesive or mechanical closure 37. The receptacle 21 is formed from an elongate rectangular blank folded along fold 35 to form the front and back walls 27, 29, respectively. In one embodiment, the blank is a plastic film such as polyethylene film having a thickness of between about 1.25 mil and about 2.0 mils. In alternative embodiments, the blank is a non-woven material or a non-woven and film laminate. The fold 35 constitutes the bottom of the receptacle 21. The front and back walls 27, 29 are sealed together as by heat seals 31s and 33s at both sides, and are free from each other at the top to define the bag opening 23. The plastic film (e.g., polyethylene) from which the bag is made is generally opaque as by being pigmented (e.g., blue) to conceal the packaged pads in the bag. In one embodiment, the closure 37 is a spot 45 of pressure-sensitive adhesive such as two-sided tape for releasably adhering the flap 25. In an alternative embodiment (not shown), the closure 37 includes a stripe of pressure-sensitive adhesive extending from side to side along the receptacle 21. The packages 11 of pads 1 (e.g., from about three to about six in number) are aligned vertically so they extend from the opening 23 to the bottom 35 of the receptacle 21. In an alternative embodiment, it is envisioned that the pads 1 may be aligned horizontally from side to side in the receptacle 21. Although the receptacle 21 may have other dimensions without departing from the scope of the present invention, in one embodiment the receptacle has an overall width measured from side to side of about 10.8 cm and an overall height measured from the opening 23 to the bottom 35 of between about 9.5 cm and about 14.0 cm. Further, the flap 25 of this one embodiment has a width matching the width of the receptacle 21 and a height of about 5.1 cm.

Thus, the supply 19 of pads 1 is carried in a hygienic condition. Because the receptacle 21 (including the flap 25) is opaque, the contents are not visible and thus are carried in a discreet manner. A pad 1 is readily available for use in hygienic condition when needed by pulling the flap 35 back (to the open condition illustrated in FIGS. 9 and 10) to open the receptacle 21, withdrawing a sealed package 11, and tearing it open to access the pad 1 therein. The torn-open package 11 is discarded. The flap 25 may then be re-adhered to the front wall 27 of the receptacle 21 to re-close the bag by means of the closure 37.

FIGS. 11 and 12 illustrate a second embodiment of the package of the present invention, designated by 47 in its entirety. The package 47 of the second embodiment again comprises an opaque plastic receptacle 49 having front and back walls 51, 53, respectively, joined at the sides 55, 57 by heat-sealed side seams, having a fold 59 for the bottom and an opening 61. Instead of the flap 25 and closure 37, the receptacle 49 is provided with conventional press-fit members 63 and 65 (i.e., conventional interlockable plastic channels) extending across the front and back walls 51, 53 adjacent the opening 61. The receptacle 49 holds a plurality (e.g., three to six) packages 11 of pads 1. Although in the illustrated embodiment the packages 11 extend vertically from the bottom 59 to adjacent the opening 61 just below the press-fit members 63, 65, it is also envisioned that the packages may extend horizontally from side to side. The press-fit members 63, 65 are conventionally used on plastic bags and will not be described in further detail. Although the receptacle 49 may have other dimensions without departing from the scope of the present invention, in one embodiment the receptacle has an overall width measured from side to side of about 10.8 cm and an overall height measured from the opening 61 to the bottom 59 of between about 9.5 cm and about 14.0 cm.

FIGS. 13 and 14 illustrate a third embodiment of the package of the present invention, designated by 67 in its entirety. For the most part, the package 67 of the third embodiment is the same as the package 47 of the second embodiment except for the use of conventional slide fastener members 69 and 71 (instead of press-fit members 63 and 65) and a conventional slide fastener 73. Members 69, 71 and slide fastener 73 are such as conventionally used on plastic bags and will not be described in further detail. Although the receptacle of the package 67 of the third embodiment may have other dimensions without departing from the scope of the present invention, in one embodiment the receptacle has an overall width measured from side to side of between about 9.5 cm and about 14.0 cm and an overall height measured from the opening to the bottom of about 10.8 cm.

FIGS. 15–17 illustrate a fourth embodiment of the package of the present invention, designated by 81 in its entirety. The package 81 of the fourth embodiment is in the style of wallet and has two pockets 83 and 85, each having an opening 83m, 85m, facing the other opening. The package 81 may be folded in half with the openings 83m, 85m on the inside. Packages 11 of pads 1 are stocked in the pockets. The package 81 comprises an elongate rectangular outside wall 87 of the opaque plastic film and inside walls 89 and 91 of said film extending across the inside face 93 of the outside wall from one side of the outside wall to the other and inward from the ends of the outside wall. Each inside wall 89, 91 terminates short of the center of the outside wall 87 thereby forming the openings 83m, 85m of a pad-containing pocket.

In further detail, the receptacle 81 comprises an elongate rectangular blank of the opaque plastic film, portions of which are folded over as indicated at 95, 97 to form the inside walls 89, 91. The folds 95, 97 form the bottoms of the pockets 83, 85. The folded-over end portions forming the inside walls 89, 91 are heat-sealed at both sides as indicated at 99 and 101 to the portion of the blank between folds 95, 97 constituting the outside wall 87. The openings of the pockets 83, 85 lie on opposite sides of a fold line F at the center of the outside wall 87 on which the receptacle is foldable as illustrated in FIG. 17. The receptacle 81 may be held closed by a tab 103 heat-sealed to the outside wall 87 and having a spot (or stripe) 105 of pressure-sensitive adhesive thereon. Or, as shown in FIG. 18, the spot (or stripe) 105 may be applied to one of the inside walls, e.g., inside wall 91 to form a package of a fifth embodiment. Although the pockets 83, 85 of the packages 81 of the fourth and fifth embodiments may have other dimensions without departing from the scope of the present invention, in one embodiment the pockets have overall widths measured from side to side of between about 9.5 cm and about 14.0 cm and overall heights measured from the respective opening to the respective bottom of between about 6.3 cm and about 8.9 cm.

Although the packages are described above as containing interlabial pads, those skilled in the art will appreciate that the packages may include other feminine care products and associated supplies. For example, the packages may contain a supply of interlabial pads and a supply of tampons and/or panty liners. Examples of associated supplies which the packages may contain include wipes and/or tissues. Further, it is envisioned that the packages may include more than one size of interlabial pad without departing from the scope of the present invention.

In view of the above, it will be seen that the several objects of the invention are achieved and other advantageous results attained.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. A package of absorbent feminine care pads for carrying a supply of the pads in hygienic condition in such manner as to maintain them in hygienic condition and to be readily available for use in hygienic condition when needed, said package comprising a receptacle, a supply of pads in the receptacle, said receptacle being in the style of a wallet having two pockets, each pocket having an opening through which a pad may be withdrawn for use when needed, said receptacle being foldable in half about a center fold line with the openings on the inside for closing the openings and for carrying the pads in hygienic condition and for continued carrying in hygienic condition of the pads remaining in the receptacle after withdrawal of a pad, wherein the package comprises an elongate rectangular outside wall of plastic film and a pair of inside walls on an inside face of the outside wall, the inside walls extending inward from an outward end of the outside wall to near the center fold line of the outside wall, thereby forming the pad-containing pockets with the openings at inner edges of the inside walls.

2. A package as set forth in claim 1 wherein the absorbent feminine care pads are individually packaged.

3. A package as set forth in claim 1 wherein said receptacle comprises an elongate rectangular blank, end portions of which are folded over to constitute said inside walls, the folds forming the bottoms of the pockets, said folded-over end portions being attached at both sides to the portion of the blank intermediate said folds, said portion constituting the outside wall.

4. A package as set forth in claim 3 wherein the blank is at least partially opaque to conceal the packaged pads in the bag.

5. A package as set forth in claim 3 wherein the blank comprises a plastic film.

6. A package as set forth in claim 1 wherein each of the absorbent feminine care pads within the supply of pads is of substantially the same size.

7. A package as set forth in claim 1 wherein only absorbent feminine care pads are positioned in the receptacle.

8. A package as set forth in claim 1 wherein the absorbent feminine care pads comprise interlabial pads.

9. A package as set forth in claim 8 wherein the interlabial pads are individually wrapped.

* * * * *